(12) United States Patent
Schulte

(10) Patent No.: US 8,603,012 B2
(45) Date of Patent: Dec. 10, 2013

(54) COMPARING HUMAN MUSCLE STRENGTH ON OPPOSITE SIDES

(75) Inventor: Alois Schulte, Melfort (CA)

(73) Assignees: Bourgault Industries Ltd., St. Brieux, Saskatchewan (CA); Alois Schulte, Melfort, Saskatchewan (CA)

( * ) Notice: Subject to any disclaimer, the term of this patent is extended or adjusted under 35 U.S.C. 154(b) by 225 days.

(21) Appl. No.: 12/640,640

(22) Filed: Dec. 17, 2009

(65) Prior Publication Data

US 2011/0093011 A1    Apr. 21, 2011

(30) Foreign Application Priority Data

Oct. 16, 2009 (CA) ..................................... 2683187

(51) Int. Cl.
*A61B 5/103* (2006.01)
*A61B 5/117* (2006.01)

(52) U.S. Cl.
USPC ............................................................. 600/587

(58) Field of Classification Search
USPC .................. 600/587, 595; 73/379.01, 379.04, 73/379.05, 379.08; 482/91–103, 110, 482/121–130, 133–138
See application file for complete search history.

(56) References Cited

U.S. PATENT DOCUMENTS

| | | | | |
|---|---|---|---|---|
| 3,752,144 A | * | 8/1973 | Weigle, Jr. | 600/587 |
| 4,805,455 A | * | 2/1989 | DelGiorno et al. | 73/379.01 |
| 5,997,440 A | * | 12/1999 | Hanoun | 482/10 |
| 2005/0245848 A1 | * | 11/2005 | Chatrenet | 600/587 |

* cited by examiner

*Primary Examiner* — Brian Szmal
*Assistant Examiner* — H. Q. Nguyen
(74) *Attorney, Agent, or Firm* — Patterson Thuente Pedersen, P.A.

(57) ABSTRACT

A muscle strength measuring apparatus has a force receiver connected to a force sensor. An upright bracing surface is rigidly positioned with respect to the force receiver to provide a testing space between the surface and the force receiver. The receiver is adjustable such that a person standing in the testing space can brace against the surface and exert a force against the force receiver with a first muscle on each side of the person's body, and can then adjust the position of the force receiver and exert a force against the force receiver with a second muscle on each side. Thus comparative strengths of muscles on opposite sides of the person's body can be accurately determined by measuring the isometric force exerted by corresponding muscles on each side.

17 Claims, 10 Drawing Sheets

COMPARING HUMAN MUSCLE STRENGTH ON OPPOSITE SIDES

RELATED APPLICATION

The present application claims priority to Canadian Application No. 2,683,187 filed Oct. 16, 2009, which is incorporated herein in its entirety by reference.

FIELD OF THE INVENTION

This invention is in the field of human kinetics and chiropractic and in particular a gauge apparatus for measuring the strength of corresponding muscles on each side of a person's body.

BACKGROUND OF THE INVENTION

Chiropractic is a system of treating disease by manipulation of the vertebral column, and is based on the premise that pain can be caused by pressure on the nerves because of faulty alignment of the bones, which prevents the nerves from transmitting to various parts of the body the neural impulses for proper functioning.

The muscles of the human body are substantially symmetric on the right and left sides of the body. This fact has led to research on the effect of unequal strength in similar muscles on right and left sides of the body. Some research has shown that such unequal strength increases the risk of injury in athletes.

Also, in chiropractic, such unequal right and left strength is thought to be an indicator of nerve interference. When it is found that a muscle or muscle group on one side is stronger than the same muscle or muscle group on the opposite side, chiropractors can treat the nerve controlling the weak muscles by manipulation and other techniques to remove pressure on the nerves or like interference which inhibits the activity of the nerves, and leads to weakness in the muscles. Successful treatment can be determined when muscle strength on each side is substantially equal.

The difference in muscle strength in the same muscles on right and left sides need not be great, and a difference of 5% can be significant. Conventional techniques and equipment have not conveniently and economically allowed for accurate determination of differential muscle strength. It is known to use hand held devices to measure strength. In one technique, the treating person pushes an air bag against the patient's arm, leg, head, or like body part and the patient's muscle resistance is measured by noting the pressure in the air bag.

Biodex Medical Systems of Shirley, N.Y., USA also makes a machine which can very accurately measure kinetic and isometric muscle strength. Most of the tests are done while the person being tested is seated. Cybex International of Medway, Mass., USA also makes machines for muscle strength testing. Such machines are however quite costly and occupy considerable space, making them impractical for wide usage.

An economical and accurate apparatus for measuring the strength in similar muscles on right and left sides of the body would allow for regular testing of, for example, athletes, industrial workers with a high potential to develop muscular skeletal problems, or who are known to have such problems, to detect such inequalities early and treat same to avoid injuries. Patients of medical professionals such as chiropractors, physiotherapists, doctors, sports trainers, and the like would benefit from the ready ability to measure right and left side muscle strength.

SUMMARY OF THE INVENTION

It is an object of the present invention to provide an apparatus for measuring the comparative strength of corresponding muscles on each side of a person's body that overcomes problems in the prior art.

In a first embodiment the present invention provides a muscle strength measuring apparatus comprising a force receiver connected to a force sensor, the force sensor operative to measure and indicate a force exerted on the force receiver. A substantially upright bracing surface is substantially rigidly positioned with respect to the force receiver with the surface oriented such that the surface and force receiver are separated by a lateral distance to provide a testing space between the surface and the force receiver. The force receiver is vertically and horizontally adjustable with respect to the surface such that a person standing in the testing space can brace against the surface and exert a force against the force receiver with a first muscle on one side of the person's body, and can then exert a force on the force receiver with a corresponding first muscle on an opposite side of the person's body, and can then adjust a position of the force receiver and exert a force against the force receiver with a second muscle on one side of the person's body, and can then exert a force on the force receiver with a corresponding second muscle on the opposite side of the person's body.

In a second embodiment the present invention provides a method of measuring comparative strengths of corresponding muscles on opposite sides of a person's body. The method comprises providing a force receiver connected to a force sensor, the force sensor operative to measure and indicate a force exerted on the force receiver; providing a substantially upright bracing surface substantially rigidly positioned with respect to the force receiver, and orienting the surface and force receiver such that a testing space is formed between the surface and the force receiver; standing in the testing space and exerting a first right force against the force receiver with a first muscle on a right side of the person's body, and then exerting a first left force on the force receiver with a corresponding first muscle on a left side of the person's body, and determining a comparative difference between the first right and left forces; and adjusting a position of the force receiver with respect to the surface and exerting a second right force against the force receiver with a second muscle on the right side of the person's body, and then exerting a second left force on the force receiver with a corresponding second muscle on the left side of the person's body, and determining a comparative difference between the second right and left forces.

The present invention provides a simple and economical apparatus and method for accurately determining comparative strengths of corresponding muscles on opposite sides of a person's body while the person is standing, thus allowing for testing of a majority of muscles in the human body. Such an economical apparatus that can be compactly stored in a small area in the corner of a room could be installed for comparative muscle testing in many locations where same would be beneficial, and where cost and space considerations are determining factors.

Although the apparatus described is optimized for comparing left and right side muscle strengths for its use in chiropractics and physiotherapy, it can also be used in a multitude of different ways to measure and record the strength of selected muscles. For example, a track and field coach may be interested in measuring the strengths of specific muscles in a group of muscles and determining the relationship of each muscle relative to the others in the group. A physiotherapist may be interested in measuring the strength of a muscle at various points over a range of motion to see how a person is recovering from an injury or responding to treatment. A personal trainer may be interested in tracking the trend of muscle strength change when using a certain weight training program or nutritional program. This invention's relatively low cost makes it possible for a whole host of potential users to apply muscle measurement to their specific fields whereas previously the costs of acquiring and operating machines to accurately do so were prohibitive.

BRIEF DESCRIPTION OF THE DRAWINGS

While the invention is claimed in the concluding portions hereof, preferred embodiments are provided in the accompanying detailed description which may be best understood in conjunction with the accompanying diagrams where like parts in each of the several diagrams are labeled with like numbers, and where:

DETAILED DESCRIPTION OF THE PREFERRED EMBODIMENTS

Figure 1:
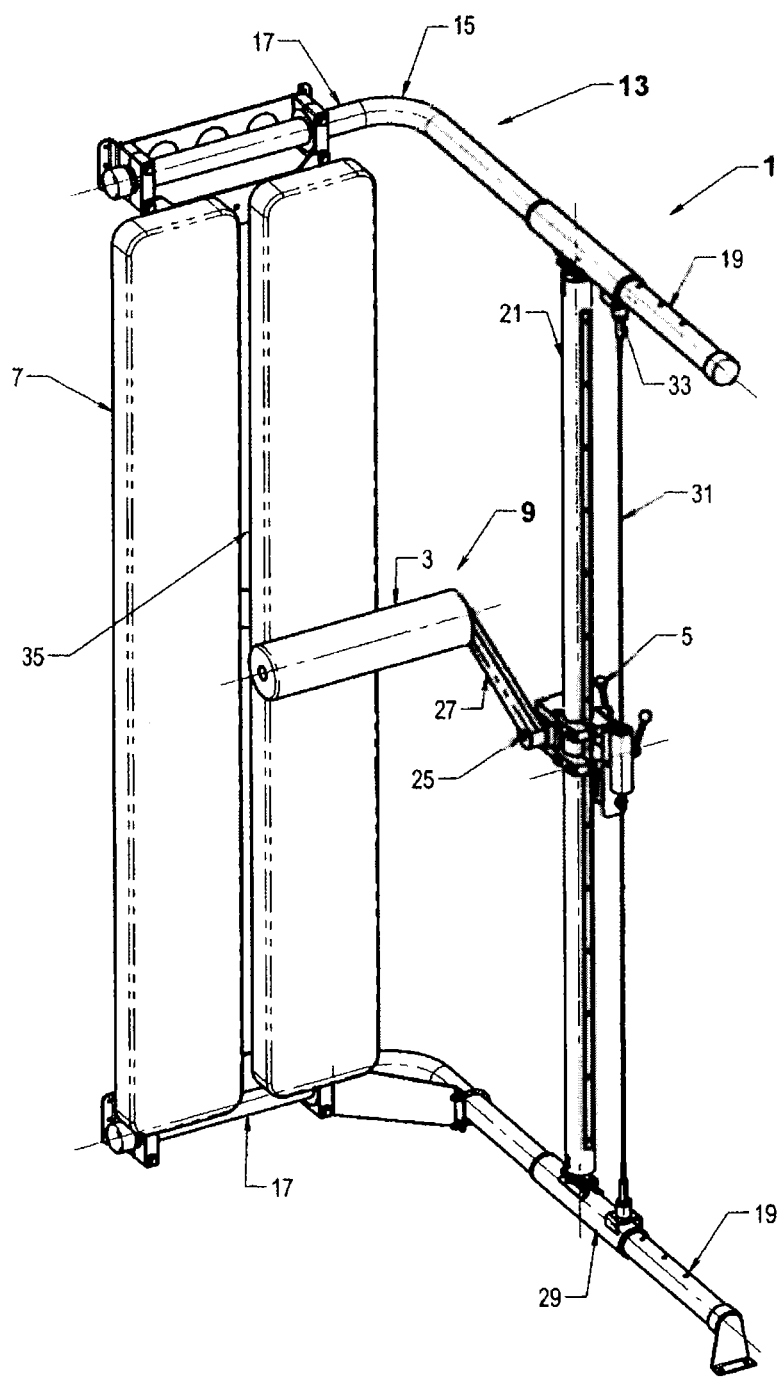
FIG. 1 is a perspective view of an embodiment of an apparatus of the present invention.

FIGS. 1-6A illustrate an embodiment of a muscle strength measuring apparatus 1 of the present invention. The apparatus 1 comprises a force receiver 3 connected to a force sensor 5. The force sensor 5 is operative to measure and indicate a force exerted on the force receiver 3. A substantially upright bracing surface, provided by backboard 7, is rigidly positioned with respect to the force receiver 3. The backboard 7 is oriented such that the surface of the backboard 7 and the force receiver 3 are separated by a lateral distance to provide a testing space 9 between the backboard 7 and the force receiver 3.

Figure 4:
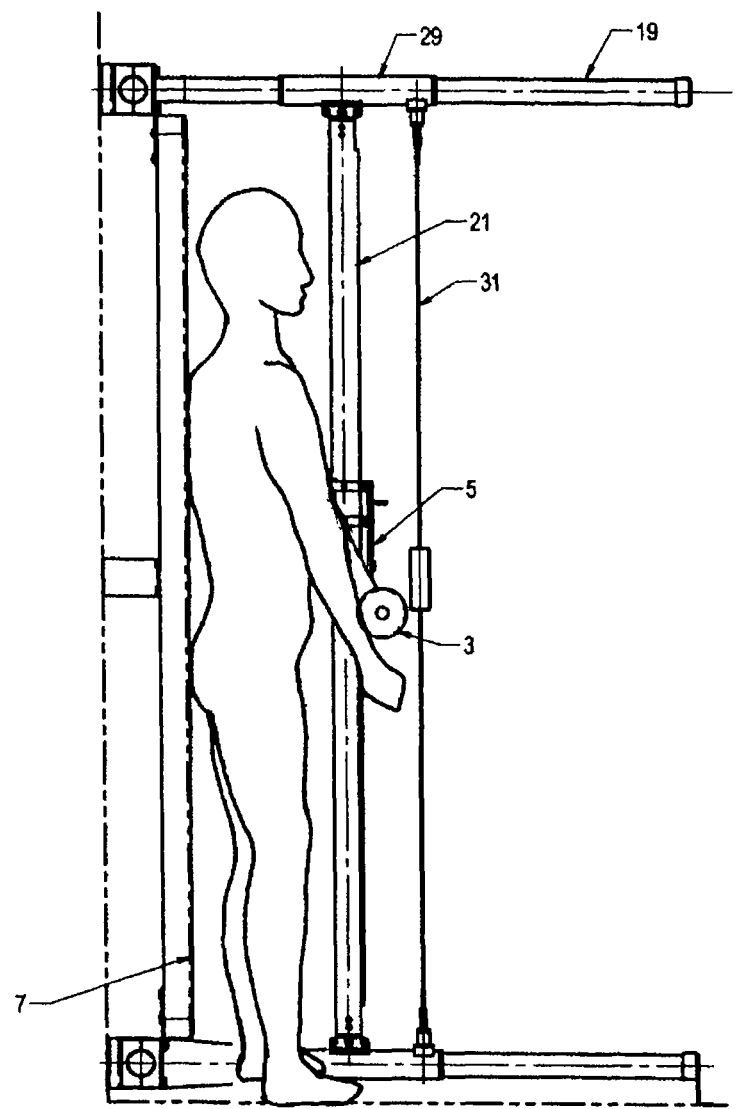
FIGS. 4 and 4A are side views of the embodiment of FIG. 1 with a person standing in the testing space and exerting a force on the force receiver with right and left arms.
Figure 4A:
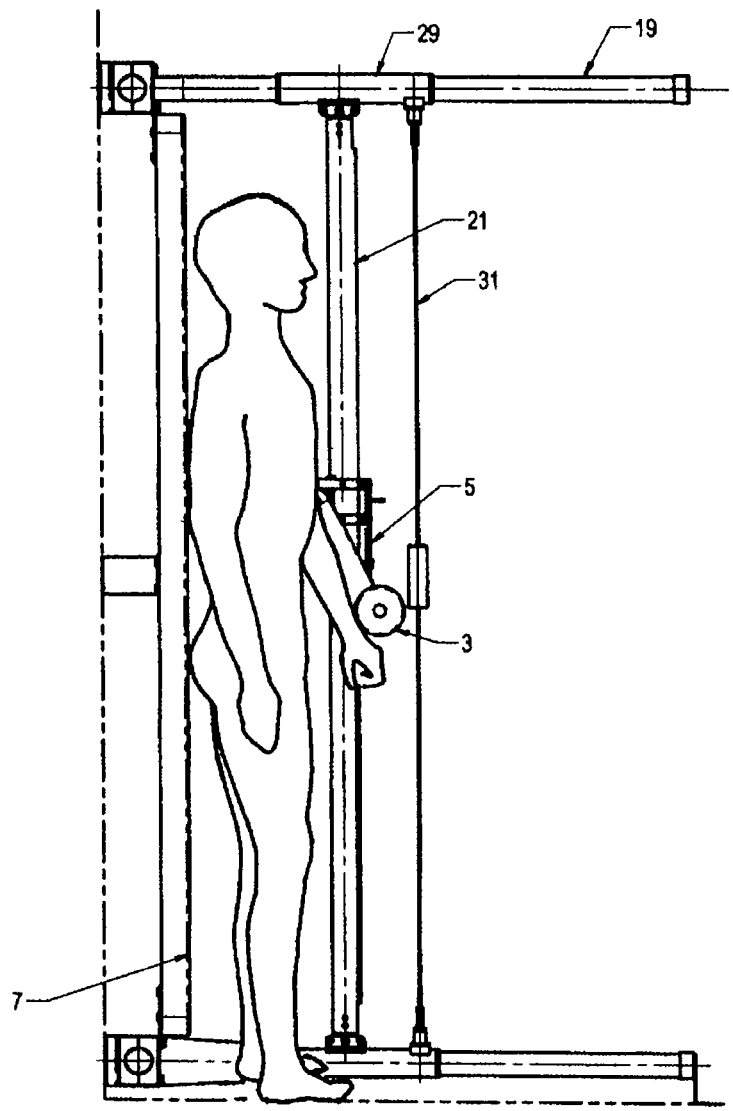

The force receiver 3 is vertically and horizontally adjustable with respect to the backboard 7 such that a person 11 standing in the testing space 9 can brace against the surface of the backboard 7 and exert a force against the force receiver 3 with a first muscle on one side of the person's body, such as the muscle moving the right arm in FIG. 4, and can then exert a force on the force receiver 3 with a corresponding first muscle on an opposite side of the person's body, such as the muscle moving the left arm in FIG. 4A.

The force receiver 3 and backboard 7 are padded for comfort. The force receiver 3 is elongated and extends substantially horizontally and parallel to the surface of the backboard 7 to define the testing space 9 between the force receiver 3 and the backboard 7. The elongated force receiver 3 has a length configured such that a person standing in the testing space 9 can exert a force on the force receiver 3 with right and left arms without moving the person's feet.

Figure 5:
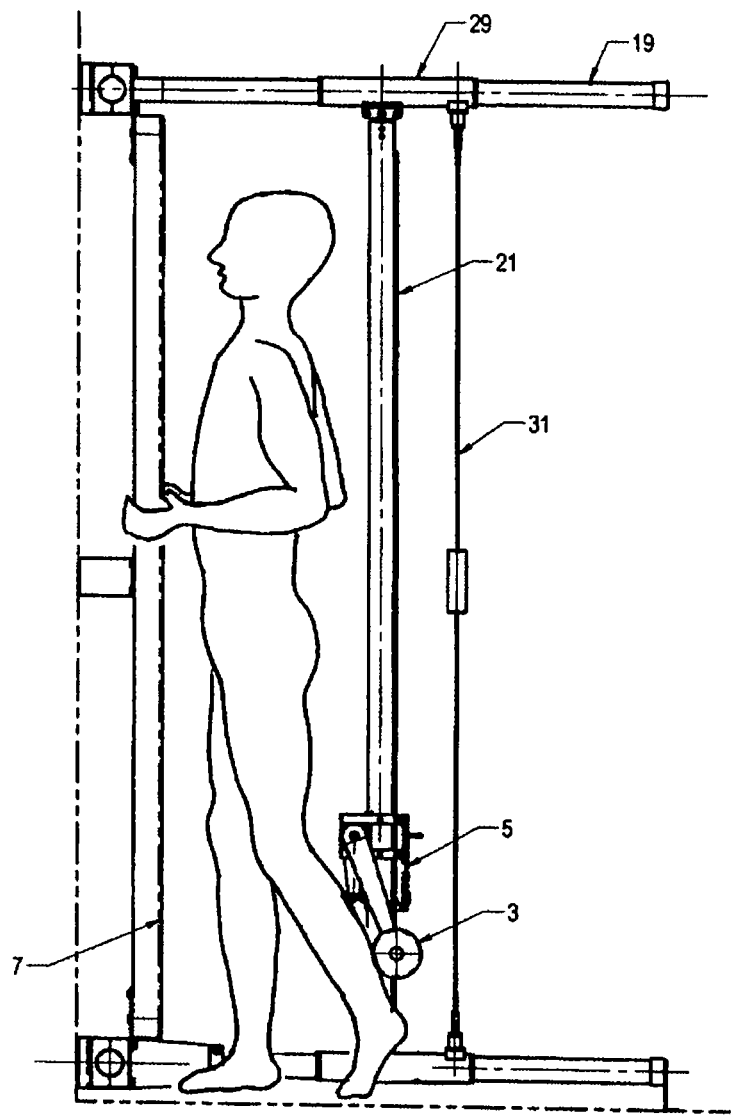
FIGS. 5 and 5A are side views of the embodiment of FIG. 1 with a person standing in the testing space and exerting a rearward force on the force receiver with right and left legs.
Figure 5A:
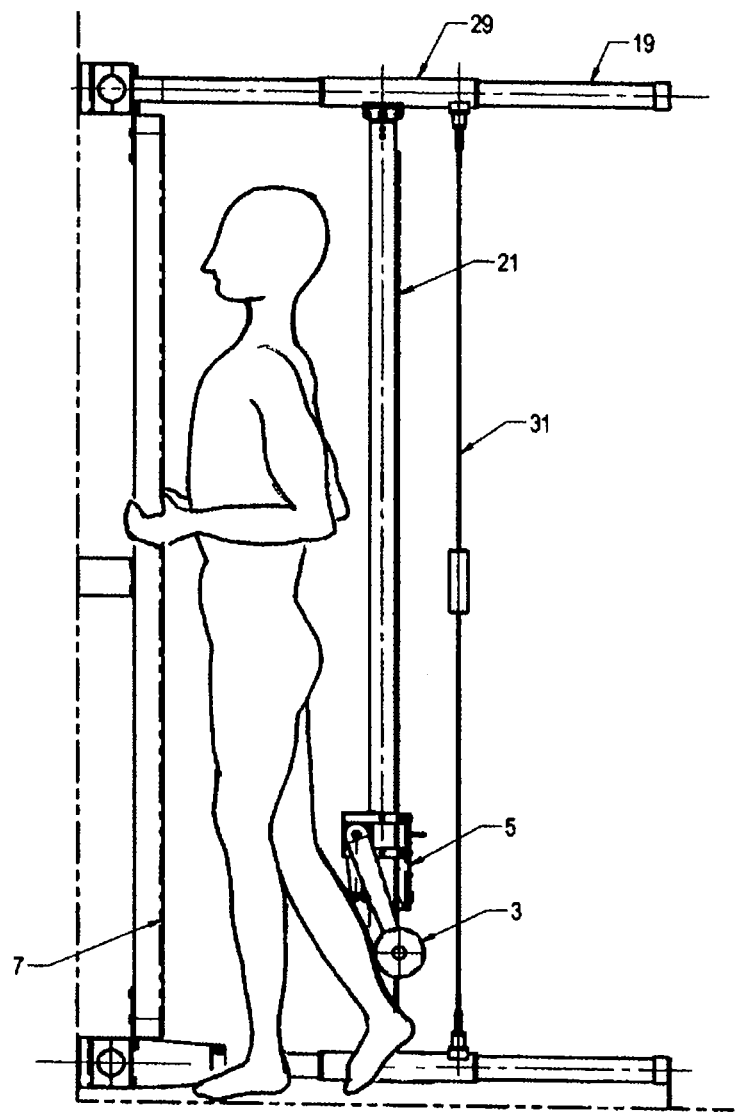

The person 11, or a test operator as the case may be, can then adjust the position of the force receiver 3 and exert a force against the force receiver with a second muscle on one side of the person's body, such as the muscle moving the left leg in FIG. 5, and can then exert a force on the force receiver 3 with a corresponding second muscle on the opposite side of the person's body, such as the muscle moving the right leg in FIG. 5A.

Figure 2:
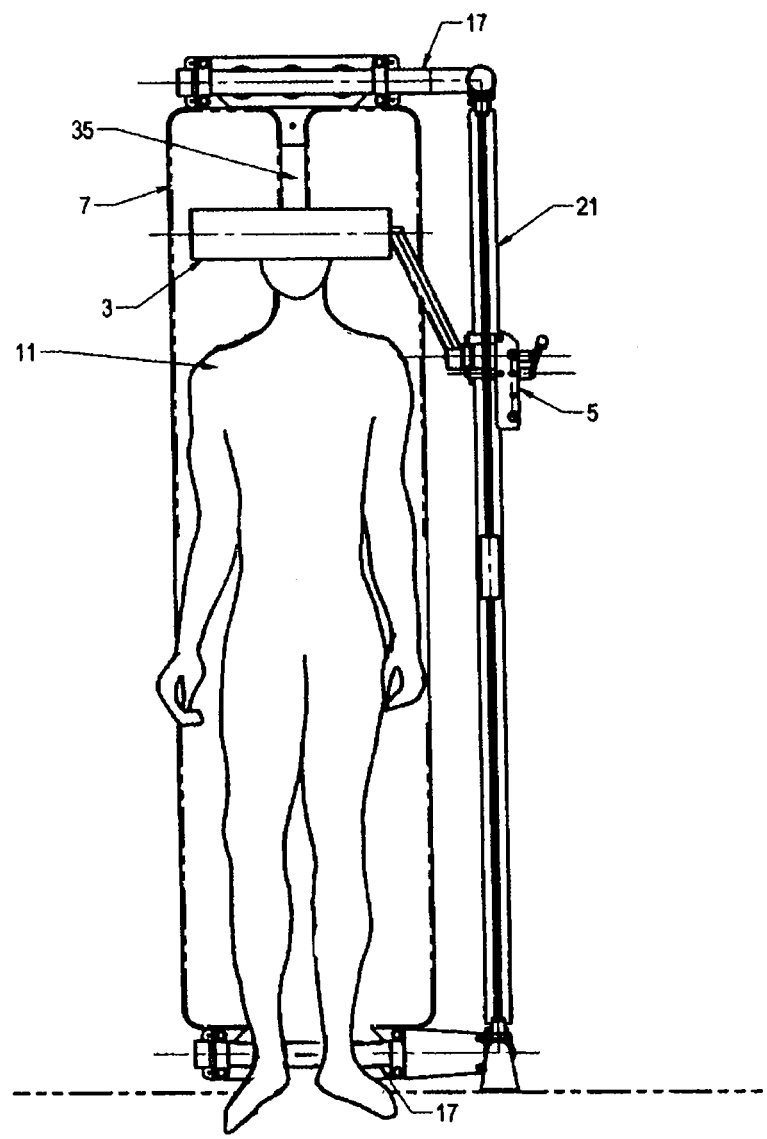
FIG. 2 is a front view of the embodiment of FIG. 1 with a person standing in the testing space and exerting a force on the force receiver with the head.
Figure 3:
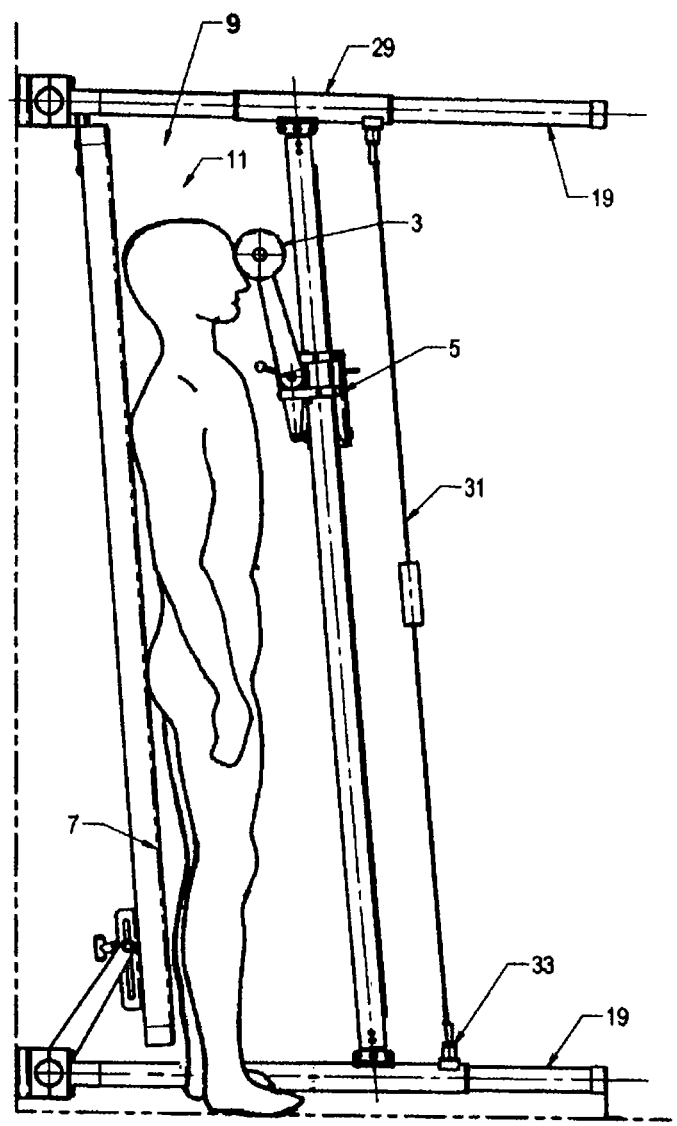
FIG. 3 is a side view of the person and embodiment shown in FIG. 2.

FIGS. 2 and 3 similarly illustrate front and side views of the apparatus 1 with the force receiver 3 positioned so the person 11 can exert a force on the force receiver 3 with the head to test neck muscle strength. While the neck muscles moving the head forward and rearward are not symmetrical, as in right and left legs and arms, it is useful to be able to conveniently test neck muscle strength, as illustrated.

Figure 6:
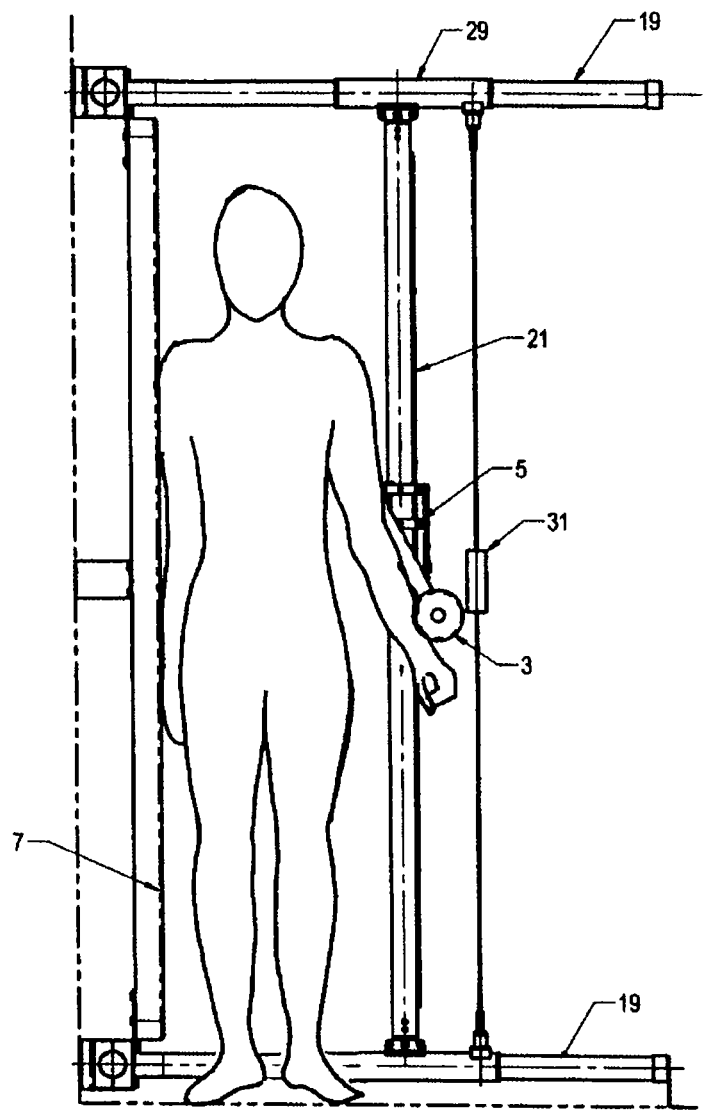
FIGS. 6 and 6A are side views of the embodiment of FIG. 1 with a person standing in the testing space and exerting an outward force on the force receiver with right and left arms.
Figure 6A:
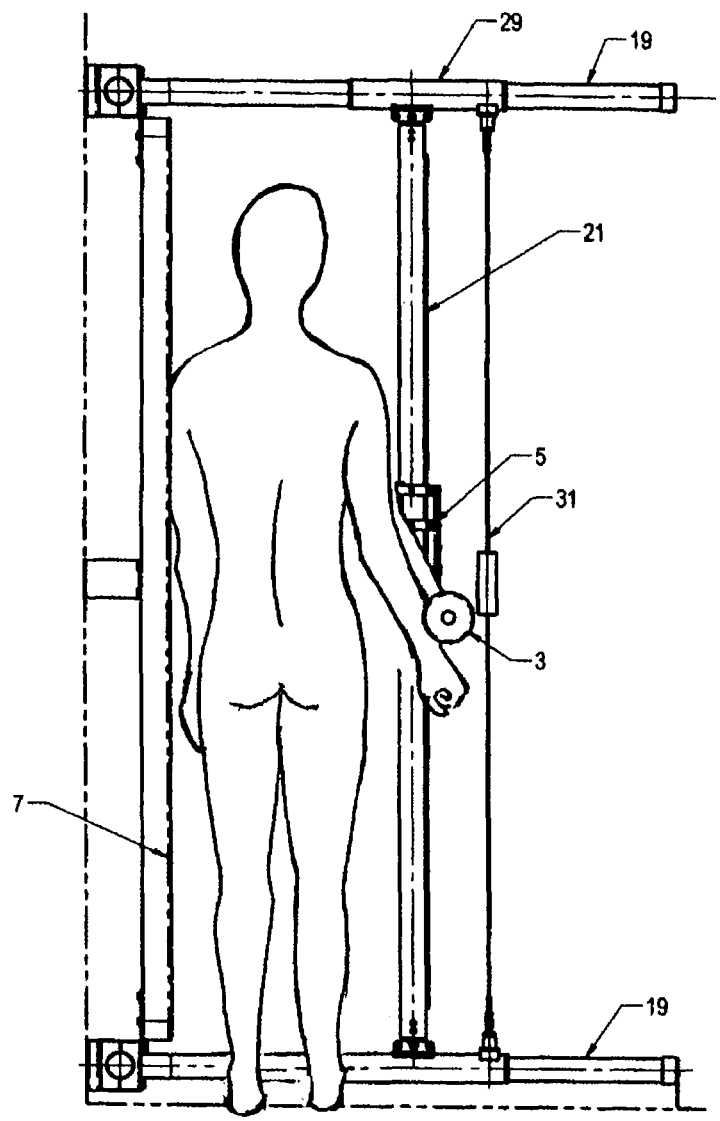

FIGS. 6 and 6A show side views of the apparatus 1 with the force receiver 3 positioned so the person 11 can exert an outward force with the left arm as seen in FIG. 6, and then turn 180 degrees and exert an outward force with the right arm as seen in FIG. 6A.

The position of the force receiver 3 can thus be varied up and down and fore and aft to test the force exerted by a variety of muscles, but once in place the position of the force receiver 3 relative to the backboard 7 is fixed, so that the forces measured are isometric forces, which are contemplated to more accurately reveal the strength of the muscle than measuring a force as the arms, legs, or neck moves through a range of motions. The padded arm of the force receiver 3 is long enough so one can measure forward and rearward forces exerted by right and left arms or legs without turning around. For lateral forces exerted by right and left arms or legs, the subject simply turns 180 degrees.

The apparatus 1 is conveniently provided by a frame 13 attachable to a fixed structure, such as the walls of a room, or the walls of a mobile vehicle or trailer that can be transported from one location to another. The bracing surface is provided by the upright oriented backboard 7 mounted to the frame 13, and the force receiver 3 is adjustably mounted to the frame 13.

In the illustrated apparatus 1, the frame 13 comprises horizontally oriented upper and lower L-shaped members 15 that are attached to the floor or walls of a room. The backboard 7 is mounted to first legs 17 of the upper and lower L-shaped members 15 such that a plane of the backboard is generally parallel to the first legs 17, and such that the inclination of the backboard 7 can be adjusted as seen in FIG. 3.

Figure 7:
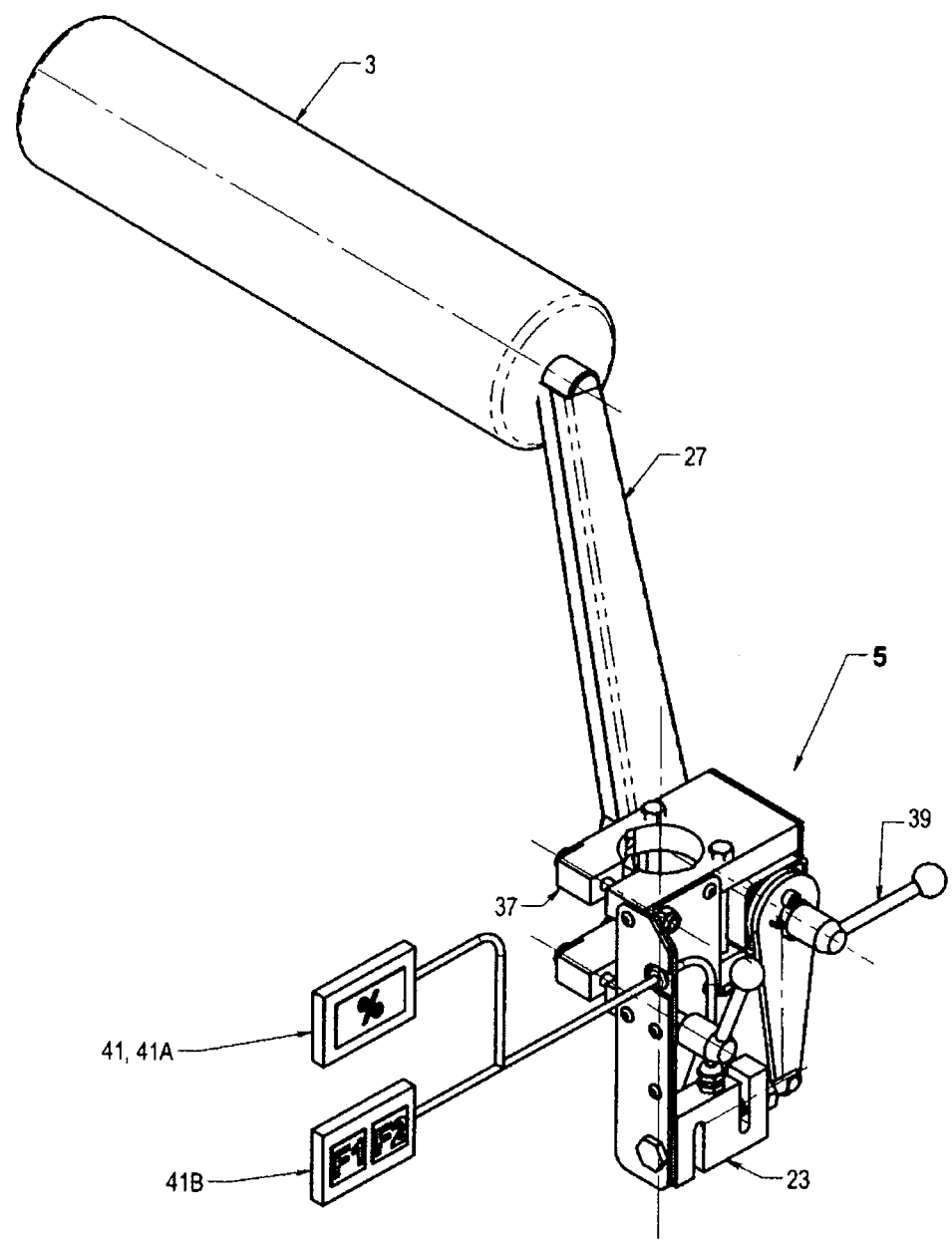
FIG. 7 is a perspective view of the force sensor and the connected force receiver of the embodiment of FIG. 1.

The force receiver 3 is mounted to an upright frame member 21 extending between second upper and lower legs 19 of the L-shaped members 15 such that the force receiver 3 extends parallel to the plane of the backboard 7 to define the testing space 9 between the force receiver 3 and the backboard 7. In the illustrated apparatus 1 the force sensor 5 comprises a strain gauge 23 as seen in FIG. 7 that is mounted on the upright member 21, and the force to be measured is applied to the strain gauge 23 through a gauge shaft 25 connected to the strain gauge 23, and the force receiver 3 is connected to the shaft 25 by a torque arm 27. The position of the torque arm 27 with respect to the shaft 25 is adjustable, such that the torque arm 27 can be rotated on the shaft 25 through 360 degrees and locked in a selected position with respect to the shaft 25 to adjust relative positions of the force receiver 3 and gauge shaft 25, and thus the relative vertical and lateral position of the force receiver 3 with respect to the upright frame member 21.

The position of the upright frame member 21 along a length of the second legs 19 of the L-shaped members 15 is adjustable. The upright frame member 21 is pivotally attached to upper and lower collars 29 that slide on the second legs 19. Cable 31 is connected to upper and lower pins 33 that engage holes spaced at intervals along the second legs 19. Pulling the cable 31 disengages the pins 33, and allows the collars 29 to be moved along the second legs 19. The bottom end of the upright frame member 21 can be positioned along a length of the second lower leg 19 independently of a position of the top end of the upright frame member 21 along a length of the second upper leg 19 so that the upright frame member 21 can be oriented substantially vertically, as seen in FIG. 4, or inclined as seen in FIG. 3.

When not in use the upright frame member 21 can be moved close to the backboard 7, with the force receiver 3 vertically aligned with the upright frame member 21 and the apparatus 1 will then occupy only a small area in the corner of a room. Such a compact apparatus 1 then could be placed in many offices or locations where space is limited.

In the illustrated apparatus 1 the backboard 7 comprises right and left flat padded surfaces 7A, 7B separated by a gap 35. The gap 35 thus provides a padded recess in a central portion of the backboard 7 configured to accommodate a person's face should a testing procedure require that the person brace his or her face against the backboard 7.

FIG. 7 illustrates the force receiver 3, torque arm 27, and force sensor 5. The force sensor 5 is attached to the upright frame member by a clamp 37, and is moved up and down by loosening or tightening the clamp with handles 39. The force sensor 5 comprises an indicator 41 connected to the strain gauge 23. The indicator is operative to indicate forces exerted on the force receiver 3.

The indicator 41A can be configured to indicate a second force exerted on the force receiver 3 as a percentage of a first force exerted on the force receiver 3. Thus the difference from one side to the other can be read directly off the indicator 41A. It is contemplated that the indicator could be configured to display the force information desired in numerous ways. For example the indicator 41B could simultaneously indicate the force F1 exerted against the force receiver 3 with the first muscle on one side of the person's body, and the force F2 exerted on the force receiver 3 with the corresponding first muscle on the opposite side of the person's body so that testing personnel can compare same.

The present invention thus provides a method of measuring comparative strengths of corresponding muscles on opposite sides of a person's body. The method comprises providing a force receiver 3 connected to a force sensor 5, the force sensor operative to measure and indicate a force exerted on the force receiver 3; providing a substantially upright bracing surface, such as backboard 7, substantially rigidly positioned with respect to the force receiver 3, and orienting the backboard 7 and force receiver 3 such that a testing space 9 is fanned between the backboard 7 and the force receiver 3; standing in the testing space 9 and exerting a first right force against the force receiver 3 with a first muscle on a right side of the person's body, and then exerting a first left force on the force receiver 3 with a corresponding first muscle on a left side of the person's body, and determining a comparative difference between the first right and left forces by reading the indicator 41; adjusting a position of the force receiver 3 with respect to the backboard 7 and exerting a second right force against the force receiver 3 with a second muscle on the right side of the person's body, and then exerting a second left force on the force receiver with a corresponding second muscle on the left side of the person's body, and determining a comparative difference between the second right and left forces by again reading the indicator 41.

The present invention thus provides a simple and relatively inexpensive apparatus for accurately determining comparative strengths of corresponding muscles on opposite sides of a person's body that, when not in use, can be stored in a small area in a corner of a room. Such an apparatus could be provided for testing in many locations where same would be beneficial.

The foregoing is considered as illustrative only of the principles of the invention. Further, since numerous changes and modifications will readily occur to those skilled in the art, it is not desired to limit the invention to the exact construction and operation shown and described, and accordingly, all such suitable changes or modifications in structure or operation which may be resorted to are intended to fall within the scope of the claimed invention.

What is claimed is:

1. A muscle strength measuring apparatus comprising:
a frame adapted for attachment to a fixed, vertical wall, the frame comprising horizontally oriented upper and lower L-shaped members, each L-shaped member comprising a horizontal first leg and a horizontal second leg perpendicular to the first leg;
a backboard mounted to first legs of the upper and lower L-shaped members such that a plane of the backboard is parallel to the first legs, and second upper and lower legs extend perpendicular to the plane of the backboard;
a force receiver mounted to an upright frame member extending between the second upper and lower legs of the L-shaped members such that the force receiver extends parallel to the plane of the backboard to define a testing space between the force receiver and the backboard;
a force sensor connected to the force receiver, the force sensor operative to measure and indicate a force exerted on the force receiver;
wherein the backboard provides a upright bracing surface rigidly positioned with respect to the force receiver, the surface oriented such that the surface and force receiver are separated by a lateral distance to provide the testing space between the surface and the force receiver;
wherein the force receiver is vertically and horizontally adjustable with respect to the surface such that when the force receiver is in a first position with respect to the surface a person standing in the testing space can brace against the surface and exert a force against the force receiver with a first muscle on one side of the person's body, and can then exert a force on the force receiver with a corresponding first muscle on an opposite side of the person's body, and can then adjust a position of the force receiver to a second position with respect to the surface and exert a force against the force receiver with a second muscle on one side of the person's body, and can then exert a force on the force receiver with a corresponding second muscle on the opposite side of the person's body; and
wherein the forces exerted against the force receiver are exerted in a direction perpendicular to the bracing surface.

2. The apparatus of claim 1 wherein the force receiver is elongated and extends horizontally and parallel to the bracing surface to define the testing space between the force receiver and the bracing surface such that the forces exerted in a first direction against the force receiver by the person create a bracing force in an opposite second direction against the bracing surface.

3. The apparatus of claim 2 wherein the elongated force receiver has a length configured such that a person standing in the testing space can exert a force on the force receiver with right and left arms.

4. The apparatus of claim 1 wherein a vertical inclination of the backboard is adjustable.

5. The apparatus of claim 1 wherein a position of the upright frame member along a length of the second legs of the L-shaped members is adjustable.

6. The apparatus of claim 5 wherein a bottom end of the upright frame member can be positioned along a length of the second lower leg of the L-shaped member independently of a position of the top end of the upright frame member along a length of the second upper leg of the L-shaped member.

7. The apparatus of claim 1 wherein a vertical position of the force receiver on the upright frame member is adjustable.

8. The apparatus of claim 7 wherein a lateral position of the force receiver on the upright frame member is adjustable.

9. The apparatus of claim 8 wherein the force sensor comprises a strain gauge mounted on the upright member at a vertically adjustable position.

10. The apparatus of claim 9 wherein force is applied to the strain gauge through a gauge shaft connected to the strain gauge, and wherein the force receiver is connected to the shaft by a torque arm.

11. The apparatus of claim 10 wherein a position of the torque arm with respect to the shaft is adjustable to adjust relative positions of the force receiver and gauge shaft.

12. The apparatus of claim 1 wherein the elongated force receiver has a length configured such that a person standing in the testing space can exert a force on the force receiver with right and left arms.

13. The apparatus of claim 1 wherein the backboard has a padded recess in a central portion thereof configured to accommodate person's face.

14. The apparatus of claim 13 wherein the backboard comprises right and left flat padded surfaces separated by a gap, and wherein the recess is provided by the gap.

15. The apparatus of claim 1 wherein the force sensor comprises an indicator operative to indicate forces exerted on the force receiver.

16. The apparatus of claim 15 wherein the indicator is operative to indicate a second force exerted on the force receiver as a percentage of a first force exerted on the force receiver.

17. The apparatus of claim 15 wherein the force sensor comprises an indicator operative to simultaneously indicate the force exerted against the force receiver with the first muscle on one side of the person's body, and the force exerted on the force receiver with the corresponding first muscle on the opposite side of the person's body.

* * * * *